United States Patent
Yim et al.

(10) Patent No.: US 11,935,232 B2
(45) Date of Patent: Mar. 19, 2024

(54) PREDICTING DISEASE PROGRESSION FROM TISSUE IMAGES AND TISSUE SEGMENTATION MAPS

(71) Applicant: Google LLC, Mountain View, CA (US)

(72) Inventors: Jason Yim, London (GB); Reena Kumari Chopra, Hounslow (GB); Terry Spitz, London (GB); Jim Huibrecht Winkens, London (GB); Annette Ada Nkechinyere Obika, London (GB); Trevor Back, Saffron Walden (GB); Joseph R. Ledsam, Tokyo (JP); Pearse A. Keane, London (GB); Jeffrey De Fauw, London (GB)

(73) Assignee: Google LLC, Mountain View, CA (US)

( * ) Notice: Subject to any disclaimer, the term of this patent is extended or adjusted under 35 U.S.C. 154(b) by 105 days.

(21) Appl. No.: 17/257,999

(22) PCT Filed: Aug. 17, 2020

(86) PCT No.: PCT/US2020/046599
§ 371 (c)(1),
(2) Date: Jan. 5, 2021

(87) PCT Pub. No.: WO2021/041068
PCT Pub. Date: Mar. 4, 2021

(65) Prior Publication Data
US 2022/0301152 A1    Sep. 22, 2022

Related U.S. Application Data

(60) Provisional application No. 62/894,562, filed on Aug. 30, 2019.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/4842* (2013.01); *A61B 5/7275* (2013.01);
(Continued)

(58) Field of Classification Search
CPC ..... G06T 7/0012; G06T 7/11; G06T 2200/04; G06T 2207/10012; G06T 2207/10101;
(Continued)

(56) References Cited

U.S. PATENT DOCUMENTS 10,192,099 B2 *   1/2019   Agaian ................. G06V 20/69
2018/0157938 A1 * 6/2018   Wang .................... G06N 3/045
(Continued)

FOREIGN PATENT DOCUMENTS

WO   WO 2018/035473        2/2018
WO   WO-2018035473 A2 *   2/2018 ............. A61B 3/145

OTHER PUBLICATIONS

Sui X et al, Choroid segmentation from Optical Coherence Tomography with graph-edge weights learned from deep convolutional neural networks, Neurocomputing 237 (2017) 332-341 (Year: 2017).*
(Continued)

*Primary Examiner* — John Villecco
*Assistant Examiner* — Kathleen M Broughton
(74) *Attorney, Agent, or Firm* — Fish & Richardson P.C.

(57) ABSTRACT

Methods, systems, and apparatus, including computer programs encoded on a computer storage medium, for generating a final progression score characterizing a likelihood that a state of a medical condition affecting eye tissue will progress to a target state in a future interval of time. In one aspect, a method comprises: obtaining: (i) an input image of eye tissue captured using an imaging modality, and (ii) a segmentation map of the eye tissue in the input image into a plurality of tissue types; providing the input image to each of one or more first classification neural networks to obtain
(Continued)

a respective first progression score from each first classification neural network; providing the segmentation map to each of one or more second classification neural networks to obtain a respective second progression score from each second classification neural network; and generating the final progression score based on the first and second progression scores.

20 Claims, 3 Drawing Sheets

(51) Int. Cl.
    *G06T 7/11*     (2017.01)
    *G06V 10/764*     (2022.01)
    *G06V 10/82*     (2022.01)

(52) U.S. Cl.
    CPC .............. *G06T 7/11* (2017.01); *G06V 10/764* (2022.01); *G06V 10/82* (2022.01); *G06T 2200/04* (2013.01); *G06T 2207/10012* (2013.01); *G06T 2207/10101* (2013.01); *G06T 2207/20021* (2013.01); *G06T 2207/20081* (2013.01); *G06T 2207/20084* (2013.01); *G06T 2207/30041* (2013.01); *G06V 2201/03* (2022.01)

(58) Field of Classification Search
    CPC . G06T 2207/20021; G06T 2207/20081; G06T 2207/20084; G06T 2207/30041; A61B 5/4842; A61B 5/7275; G06V 10/764; G06V 10/82; G06V 2201/03
    See application file for complete search history.

(56) References Cited

U.S. PATENT DOCUMENTS

| | | | | |
|---|---|---|---|---|
| 2018/0315193 A1* | 11/2018 | Paschalakis | ......... | G06V 40/193 |
| 2019/0005684 A1* | 1/2019 | De Fauw | .............. | G06T 11/003 |
| 2019/0110753 A1 | 4/2019 | Kang et al. | | |
| 2020/0160032 A1* | 5/2020 | Allen | ...................... | G16H 50/30 |
| 2023/0342929 A1* | 10/2023 | Kim | .......................... | G06N 3/08 |

OTHER PUBLICATIONS

Soomro T et al, The use of optical coherence tomography angiography for detecting choroidal neovascularization, compared to standard multimodal imaging, Eye (2018) 32, 661-672. (Year: 2018).*

Tang et al, Neovascularization Detection and Localization in Fundus Images Using Deep Learning, 2021, Sensors, 21(5327): pp. 1-18 (Year: 2021).*

Xu et al, Hybrid Global-Local Representation CNN Model for Automatic Cataract Grading, 2019, IEEE J. BME and Health Informatics, 24(2): 556-568. (Year: 2019).*

PCT International Preliminary Report on Patentability in International Application No. PCT/US2020/046599, dated Mar. 10, 2022, 10 pages.

Abadi et al., "TensorFlow: Large-Scale Machine Learning on Heterogeneous Distributed Systems," Mar. 2016, 19 pages.

Abdelfattah et al., "Drusen volume as a predictor of disease progression in patients with late age-related macular degeneration in the fellow eye," Investigative Ophthalmology & Visual Science, Apr. 2016, 57(4):1839-46.

Age-Related Eye Disease Study Research Group, "A simplified severity scale for age-related macular degeneration: AREDS report No. 18. Archives of ophthalmology," Nov. 2005, 123(11):1570.

Age-Related Eye Disease Study Research Group, "Risk factors associated with age-related macular degeneration: a case-control study in the age-related eye disease study: age-related eye disease study report number," Ophthalmology, Dec. 2000, 107(12):2224-32.

Age-Related Eye Disease Study Research Group, "The Age-Related Eye Disease Study system for classifying age-related macular degeneration from stereoscopic color fundus photographs: the Age-Related Eye Disease Study Report No. 6," American Journal of Ophthalmology, Nov. 2001, 132(5):668-81.

Amoaku et al., "Optimising patient management: act now to ensure current and continual delivery of best possible patient care," Eye, Feb. 2012, 26(1):S2-1.

Ardila et al., "End-to-end lung cancer screening with three-dimensional deep learning on low-dose chest computed tomography," Nature medicine, Jun. 2019, 25(6):954-61.

Babenko et al., "Predicting progression of age-related macular degeneration from fundus images using deep learning," arXiv preprint arXiv:1904.05478, Apr. 2019, 67 pages.

Balaratnasingam et al., "Associations between retinal pigment epithelium and drusen volume changes during the lifecycle of large drusenoid pigment epithelial detachments," Investigative ophthalmology & visual science, Oct. 2016, 57(13):5479-89.

Balaratnasingam et al., "Clinical characteristics, choroidal neovascularization, and predictors of visual outcomes in acquired vitelliform lesions," American Journal of Ophthalmology, Dec. 2016, 172:28-38.

Banerjee et al., "A deep-learning approach for prognosis of age-related macular degeneration disease using SD-OCT imaging biomarkers," arXiv preprint arXiv:1902.10700, Feb. 2019, 20 pages.

Bek et al., "Incidence and risk factors for neovascular age-related macular degeneration in the fellow eye," Graefe's Archive for Clinical and Experimental Ophthalmology, Nov. 2018, 256(11):2061-8.

Bogunović et al., "Machine learning of the progression of intermediate age-related macular degeneration based on OCT imaging," Investigative ophthalmology & visual science, May 2017, 58(6):BIO141-50.

Bressler et al., "Relationship of drusen and abnormalities of the retinal pigment epithelium to the prognosis of neovascular macular degeneration," Archives of Ophthalmology, Oct. 1990, 108(10):1442-7.

Buchlovsky et al., "TF-Replicator: Distributed Machine Learning for Researchers," Feb. 2019, 12 pages.

Campochiaro et al., "The Port Delivery System with Ranibizumab for Neovascular Age-Related Macular Degeneration: Results from the Randomized Phase 2 Ladder Clinical Trial," Ophthalmology, Aug. 2019, 126(8):1141-1154.

Carnevali et al., "Natural history of treatment-naïve quiescent choroidal neovascularization in age-related macular degeneration using OCT angiography," Ophthalmology Retina, Sep. 2018, 2(9):922-30.

Chew et al., "Summary results and recommendations from the age-related eye disease study," Archives of ophthalmology, Dec. 2009, 127(12):1678-9.

Christenbury et al., "Progression of Macular Atrophy in Eyes With Type 1 Neovascularization and Age-Related Macular Degeneration Receiving Long-Term Intravitreal Anti-Vascular Endothelial Growth Factor Therapy," An Optical Coherence Tomographic Angiography Analysis, 2018, 1276-1288.

Cicek et al., "3D U-Net: Learning Dense Volumetric Segmentation from Sparse Annotation," Medical Image Computing and Computer-Assisted Intervention—MICCAI 2016 424-432, 2016, 9 pages.

Clemons et al., "Risk factors for the incidence of advanced age-related macular degeneration in the Age-Related Eye Disease Study (AREDS) AREDS report No. 19." Ophthalmology, Apr. 2005, 112(4):533-9.

Cohen et al., "Prevalence of reticular pseudodrusen in age-related macular degeneration with newly diagnosed choroidal neovascularisation," British journal of ophthalmology, Mar. 2007, 91(3):354-9.

Curcio et al., "Activated retinal pigment epithelium, an optical coherence tomography biomarker for progression in age-related macular degeneration," Investigative ophthalmology & visual science, May 2017, 58(6):BIO211-26.

(56) References Cited

OTHER PUBLICATIONS

De Fauw et al., "Automated analysis of retinal imaging using machine learning techniques for computer vision," F1000Res, Jul. 2016, 8 pages.

De Fauw et al., "Clinically applicable deep learning for diagnosis and referral in retinal disease," Nature medicine, Sep. 2018, 24(9):1342-50.

De Oliveira et al., "Natural history of subclinical neovascularization in nonexudative age-related macular degeneration using swept-source OCT angiography," Ophthalmology, Feb. 2018, 125(2):255-66.

DeepMind.com [online], "Open sourcing Sonnet-a new library for constructing neural network," Apr. 2017, retrieved on Jan. 13, 2021, retrieved from URL<https://deepmind.com/blog/article/open-sourcing-sonnet, 5 pages.

Dugel et al., "Hawk and Harrier: phase 3, multicenter, randomized, double-masked trials of brolucizumab for neovascular age-related macular degeneration," Ophthalmology, Jan. 2020, 127(1):72-84.

Esteva et al., Dermatologist-level classification of skin cancer with deep neural networks, Nature, Feb. 2017, 542(7639):115-8.

Ezzati et al., "Comparative quantification of mortality and burden of disease attributable to selected risk factors," Global burden of disease and risk factors, Jan. 2006, 1;2:241-396.

Fasler et al., "Moorfields AMD database report 2: fellow eye involvement with neovascular age-related macular degeneration," British Journal of Ophthalmology, May 2020, 104(5):684-90.

Folgar et al., "Drusen volume and retinal pigment epithelium abnormal thinning volume predict 2-year progression of age-related macular degeneration," Ophthalmology, Jan. 2016, 123(1):39-50.

Folgar et al., "Spatial correlation between hyperpigmentary changes on color fundus photography and hyperreflective foci on SDOCT in intermediate AMD," Investigative ophthalmology & visual science, Jul. 2012, 53(8):4626-33.

Fragiotta et al., "Predictive factors for development of neovascular age-related macular degeneration: a spectral-domain optical coherence tomography study," Retina, Feb. 2018, 38(2):245-52.

Graham et al., "Anonymisation: managing data protection risk code of practice," Information Commissioner's Office, 2012.

Hinton et al., "Distilling the knowledge in a neural network," arXiv preprint arXiv:1503.02531, Mar. 2015, 9 pages.

Huang et al., "Densely connected convolutional networks: IEEE Conference on Computer Vision and Pattern Recognition," Densely Connected Convolutional Networks—IEEE Conference Publication, 2017, 9 pages.

IAI Versus Sham as Prophylaxis Against Conversion to Neovascular Amd (Pro-Con):ClinicalTrials.gov Identifier:NCT02462889, ClinicalTrials.gov available at: https://clinicaltrials.gov/ct2/show/nct02462889.

Jager et al., "Age-related macular degeneration," New England Journal of Medicine, Jun. 2008, 358(24):2606-17.

Klein et al., "The five-year incidence and progression of age-related maculopathy: the Beaver Dam Eye Study," Ophthalmology, Jan. 1997 104(1):7-21.

Krause et al., "Grader variability and the importance of reference standards for evaluating machine learning models for diabetic retinopathy," Ophthalmology, Aug. 2018, 125(8):1264-72.

Lee et al., "Neovascularization in Fellow Eye of Unilateral Neovascular Age-related Macular Degeneration According to Different Drusen Types," Am J Ophthalmol, Dec. 2019, 208:103-110.

Lek et al., "Interpretation of subretinal fluid using OCT in intermediate age-related macular degeneration," Ophthalmology Retina, Aug. 2018, 2(8):792-802.

Lim et al., "Delay to treatment and visual outcomes in patients treated with anti-vascular endothelial growth factor for age-related macular degeneration," American journal of ophthalmology, Apr. 2012, 153(4):678-86.

Machinelearningmastery.com [online], "Ensemble Learning Methods for Deep Learning Neural Networks," Apr. 2017, retrieved on Jan. 12, 2021, retrieved from URL<https://machinelearningmastery.com/ensemble-methods-for-deep-learning-neural-networks/, 19 pages.

Maguire et al., "Incidence of choroidal neovascularization in the fellow eye in the comparison of age-related macular degeneration treatments trials," Ophthalmology, Oct. 2013, 120(10):2035-41.

Muether et al., "Delay between medical indication to anti-VEGF treatment in age-related macular degeneration can result in a loss of visual acuity," Graefes Arch Clin Exp Ophthalmol, May 2011, 249(5):633-7.

NIHR Oxford Biomedical Research Centre [online], "World's First Gene Therapy Operation for Common Cause of Sight Loss Carried Out," retrieved on Jan. 13, 2021, retrieved from URL<https://oxfordbrc.nihr.ac.uk/worlds-first-gene-therapy-operation-for-common-cause-of-sight-loss-carried-out/ (2019), 5 pages.

Owen et al., "The estimated prevalence and incidence of late stage age related macular degeneration in the UK, " British Journal of Ophthalmology, May 2012, 96(5):752-6.

PCT International Search Report and Written Opinion in International Appln. No. PCT/US2020/046599, dated Nov. 2, 2020, 17 pages.

Poplin et al., "Prediction of cardiovascular risk factors from retinal fundus photographs via deep learning," Nature Biomedical Engineering, Mar. 2018, 2(3):158.

Prophylactic Ranibizumab for Exudative Age-related Macular Degeneration (Prevent):ClinicalTrials.gov Identifier:NCT02140151. ClinicalTrials.gov available at: https://clinicaltrials.gov/ct2/show/nct02140151.

Rein et al., "Forecasting age-related macular degeneration through the year 2050: the potential impact of new treatments," Archives of ophthalmology, Apr. 2009, 127(4):533-40.

Roisman et al., "Optical coherence tomography angiography of asymptomatic neovascularization in intermediate age-related macular degeneration," Ophthalmology, Jun. 2016, 123(6):1309-19.

Rudnicka et al., "Incidence of late-stage age-related macular degeneration in American whites: systematic review and meta-analysis," American journal of ophthalmology, Jul. 2015, 160(1):85-93.

Russakoff et al., "Deep learning for prediction of AMD progression: a pilot study," Investigative ophthalmology & visual science, Feb. 2019, 60(2):712-22.

Sadda et al., "Consensus Definition for Atrophy Associated with Age-Related Macular Degeneration on OCT: Classification of Atrophy Report," Ophthalmology, 2018, 537-548.

Sahni et al., "Simultaneous inhibition of angiopoietin-2 and vascular endothelial growth factor-A with faricimab in diabetic macular edema: Boulevard phase 2 randomized trial," Ophthalmology, Aug. 2019 126(8):1155-70.

Schmidt-Erfurth et al., "Prediction of individual disease conversion in early AMD using artificial intelligence," Investigative ophthalmology & visual science, Jul. 2018, 59(8):3199-208.

Tham et al., "Global prevalence of glaucoma and projections of glaucoma burden through 2040: a systematic review and meta-analysis," Ophthalmology, Nov. 2014, 121(11):2081-90.

Tomašev et al., "A clinically applicable approach to continuous prediction of future acute kidney injury," Nature, Aug. 2019, 572(7767):116-9.

Tonekaboni et al., What clinicians want: contextualizing explainable machine learning for clinical end use, arXiv preprint arXiv:1905.05134, May 2019, 21 pages.

Ttowardsdatascience.com [online], "Test Time Augmentation (TTA) and how to perform it with Keras," Feb. 2019, retrieved on Jan. 12, 2021, retrieved from URL<https://towardsdatascience.com/test-time-augmentation-tta-and-how-to-perform-it-with-keras-4ac19b67fb4d, 8 pages.

VanderBeek et al., "Racial differences in age-related macular degeneration rates in the United States: a longitudinal analysis of a managed care network," American journal of ophthalmology, Aug. 2011, 152(2):273-82.

Veerappan et al., "Optical coherence tomography reflective drusen substructures predict progression to geographic atrophy in age-related macular degeneration," Ophthalmology, Dec. 2016, 123(12):2554-70.

Wong et al., "Global prevalence of age-related macular degeneration and disease burden projection for 2020 and 2040: a systematic review and meta-analysis," The Lancet Global Health, Feb. 2014, 2(2):e 106-16.

(56) References Cited

OTHER PUBLICATIONS

Yim et al., "Predicting conversion to wet age-related macular degeneration using deep learning," Nature Medicine May 2020, 18 pages.
Zarranz-Ventura et al., "The neovascular age-related macular degeneration database: report 2: incidence, management, and visual outcomes of second treated eyes," Ophthalmology, Oct. 2014, 121(10):1966-75.
Zhao et al., "Bottom-up temporal action localization with mutual regularization," European Conference on Computer Vision, Aug. 2020, 539-555.
Zhou et al., "Comparison of Age-Related Macular Degeneration Treatments Trials Research Group Pseudodrusen and incidence of late age-related macular degeneration in fellow eyes in the comparison of age-related macular degeneration treatments trials," Ophthalmology, Jul. 2016, 1;123(7):1530-40.
Zweifel et al., "Prevalence and significance of subretinal drusenoid deposits (reticular pseudodrusen) in age-related macular degeneration," Ophthalmology, Sep. 2010, 117(9):1775-81.
Office Action in Indian Appln. No. 202227001467, dated Jun. 15, 2022, 6 pages (with English Translation).

\* cited by examiner

PREDICTING DISEASE PROGRESSION FROM TISSUE IMAGES AND TISSUE SEGMENTATION MAPS

CROSS-REFERENCE TO RELATED APPLICATION

This application is a National Stage Application under 35 U.S.C. § 371 and claims the benefit of International Application No. PCT/US2020/046599, filed Aug. 17, 2020, which claims priority to U.S. Application No. 62/894,562, filed Aug. 30, 2019, the disclosure of which is incorporated herein by reference.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification generally describes a system implemented as computer programs on one or more computers in one or more locations that processes a tissue image depicting tissue in a region of the body of a patient to generate a progression score for a medical condition affecting the tissue. Throughout this specification, a "progression score" may refer to a numerical value that characterizes a likelihood that the state of the medical condition affecting the tissue will progress to a target state in a future interval of time. The future interval of time may be, e.g., an interval of time having a specified duration starting from a "current" time point, e.g., the time point when the tissue image was captured.

According to a first aspect there is provided a system comprising one or more computers and one or more storage devices storing instructions that when executed by the one or more computers cause the one or more computers to implement one or more first classification neural networks, one or more second classification neural networks, and a subsystem.

Each first classification neural network is configured to receive an image of eye tissue captured using an imaging modality, and process the image to generate a first progression score characterizing a likelihood that a state of a medical condition affecting the eye tissue will progress to a target state in a future interval of time. Each second classification neural network is configured to receive a segmentation map of an image of eye tissue that segments the eye tissue in the image into a plurality of tissue types, and process the segmentation map to generate a second progression score characterizing a likelihood that a state of a medical condition affecting the eye tissue will progress to a target state in a future interval of time. The subsystem is configured to obtain: (i) an input image of eye tissue captured using an imaging modality, and (ii) a segmentation map of the eye tissue in the input image into a plurality of tissue types, and generate, based on the input image and the segmentation map, a final progression score characterizing a likelihood that a state of a medical condition affecting the eye tissue will progress to a target state in a future interval of time, by providing the input image to each of the first classification neural networks to obtain a respective first progression score from each first classification neural network, providing the segmentation map to each of the second classification neural networks to obtain a respective second progression score from each second classification neural network, and generating the final progression score based on the first progression scores and the second progression scores.

Some advantages of this approach are described later, but in broad terms it has been found that the first and second classification neural networks, one working on a "raw" image of the eye tissue, the other working on a tissue segmentation map, complement one another's performance when processing representations of eye tissue to identify when a medical condition will progress.

As described, a likelihood of progression of the medical condition is characterized by the final progression score. Looked at differently the final progression score may be considered as evaluating a condition of the eye tissue, in particular where the evaluation determines whether the eye has pathology which indicates that progression to the target state is likely (e.g. above a treatment threshold) within the future interval of time. The system may determine, based on the final progression score, that treatment, e.g. preventative treatment, should be administered to the eye tissue.

In implementations of the system the medical condition affecting the eye tissue is age-related macular degeneration (AMD), in particular dry AMD. In implementations the target state of the medical condition affecting the eye tissue is neovascular age-related macular degeneration (nAMD), also referred to as exudative AMD (exAMD) or wet AMD. In some applications the medical condition is (dry) AMD in the eye of a patient where the patient's other (fellow) eye has been diagnosed as having wet AMD (i.e. nAMD or exAMD) and the target state is wet AMD.

The image of the eye tissue captured and processed by the first classification neural network(s) may be an optical coherence tomography (OCT) image, but this is not essential and the image of the eye tissue may be captured using other techniques. The image may, but need not be, be a three-dimensional image comprising a plurality of voxels.

The segmentation map may be generated manually but in implementations the system may include one or more segmentation neural networks. Each segmentation neural network may be configured to receive an image of eye tissue captured using the imaging modality, and process the image to generate a segmentation map of the image that segments the eye tissue in the image into a plurality of tissue types. Where there is more than one segmentation neural network the subsystem may be configured to provide the input image to each of the segmentation neural networks to obtain a respective initial segmentation map of the eye tissue in the input image into the plurality of tissue types from each segmentation neural network, and generate the segmentation map based on the initial segmentation maps e.g. by averaging.

In implementations the first and second classification neural network(s) may be trained to generate additional outputs characterizing referral decisions and additional diagnoses. Such outputs may be used when training the system and afterwards disregarded. A referral decision may be a decision (of a clinician) defining a need for further medical attention for a patient with the medical condition e.g. specifying an urgency with which the patient should receive further medical attention. An additional diagnosis may be a diagnosis of a pathology of the imaged eye in addition to the medical condition, e.g. in addition to AMD.

In some implementations, each segmentation neural network is a convolutional neural network having a U-Net architecture.

In some implementations, the input image of eye tissue captured using the imaging modality is a three-dimensional image comprising a plurality of voxels, and the segmentation map assigns a respective tissue type from a predetermined set of tissue types to each of the voxels.

In some implementations, the predetermined set of tissue types comprise one or more anatomical tissue types and one or more pathological tissue types.

In some implementations, the future interval of time is an interval of time starting from a current time point.

In some implementations, the system performs operations further comprising generating, for each of a plurality of given future intervals of time, a respective final progression score characterizing a likelihood that the state of the medical condition affecting the eye tissue will progress to the target state in the given future interval of time.

In some implementations, the system performs operations further comprising determining, based on the final progression score, that preventative treatment should be administered to the eye tissue.

In some implementations, the first classification neural networks and the second classification neural networks are trained to generate additional outputs characterizing referral decisions and additional diagnoses.

In some implementations, the system comprises a plurality of first classification neural networks, wherein each first classification neural network has a same architecture but has been trained (i) on a different set of training data, (ii) with differently initialized parameters, or (iii) both, from each other first classification neural network.

In some implementations, the system comprises a plurality of second classification neural networks, wherein each second classification neural network has a same architecture but has been trained (i) on a different set of training data, (ii) with differently initialized parameters, or (iii) both, from each other second classification neural network.

In some implementations, providing the input image to each of the first classification neural networks and providing the segmentation map to each of the second classification neural networks comprises performing test-time data augmentation.

In some implementations, generating the final progression score based on the first progression scores and the second progression scores comprises averaging the first progression scores and the second progression scores.

According to another aspect there is provided a computer-implemented method comprising the operations of the system described herein.

According to another aspect there are provided one or more non-transitory computer storage media storing instructions that when executed by one or more computers cause the one or more computers to perform the operations of the system described herein.

Particular embodiments of the subject matter described in this specification can be implemented so as to realize one or more of the following advantages.

The system described in this specification can predict the progression of a medical condition affecting a patient. For example, the system can be used to predict whether an early, mild form of age-related macular degeneration (AMD) affecting an eye of a patient will convert to sight-threatening neovascular AMD (nAMD) or exudative wet AMD (ex-AMD) in a 6-month time period. Therefore the system can be used to facilitate effective provision of medical care, e.g., by identifying patients who should receive preventative medical treatments, or by identifying patients where regular follow-ups are necessary to closely monitor progression of a medical condition.

As part of generating a progression score characterizing the predicted progression of a medical condition in a patient, the system receives a tissue (anatomical) image showing a region of the body of the patient, and generates a segmentation map that segments the tissue image into multiple tissue classes. The system then processes the tissue image to generate one or more respective progression scores, processes the segmentation map to generate one or more respective progression scores, and ensembles (i.e., combines) all the generated progression scores to generate a final progression score. The progression scores generated based on the tissue image and the progression scores generated based on the segmentation map may be different and complementary. For example, the progression scores generated based on the tissue image may reflect image features not captured by the segmentation map that may be relevant to the progression prediction task, e.g., patterns in the reflectivity of the tissue in an OCT image of an eye. The progression scores generated based on the segmentation map may be more stable (i.e., less likely to assume inaccurate outlier values) than those generated using the tissue image, e.g., because of the potentially lower complexity of the segmentation map relative to the tissue image. Therefore, generating the final progression score based on both the tissue image and the segmentation map may improve the performance, e.g., the accuracy and robustness, of the system.

The segmentation maps generated by the system may provide a user of the system with a clinically interpretable indication of some of the evidence used by the system in generating its predictions, which can enable the user to assess the reliability of the predictions. In contrast, some conventional systems operate as "black boxes" that do not reveal any insight into how predictions are generated.

The system can generate a final progression score characterizing the predicted progression of disease in a patient by combining a collection of progression scores (in some cases, hundreds of progression scores) made by respective progression classification neural networks that have been trained differently, that process different inputs, or both. This can enable the system to generate final progression scores that are stable and reliable, thereby making the system more appropriate for deployment in clinical workflows. Moreover, since the progression scores generated by the progression classification neural networks are aggregated, the system may train each progression classification neural network on a lesser amount of training data than might otherwise be required while maintaining the overall accuracy of the system. Therefore, the system may use less memory to store the training data used to train the progression classification neural networks, thereby reducing use of memory resources in comparison to some other systems.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
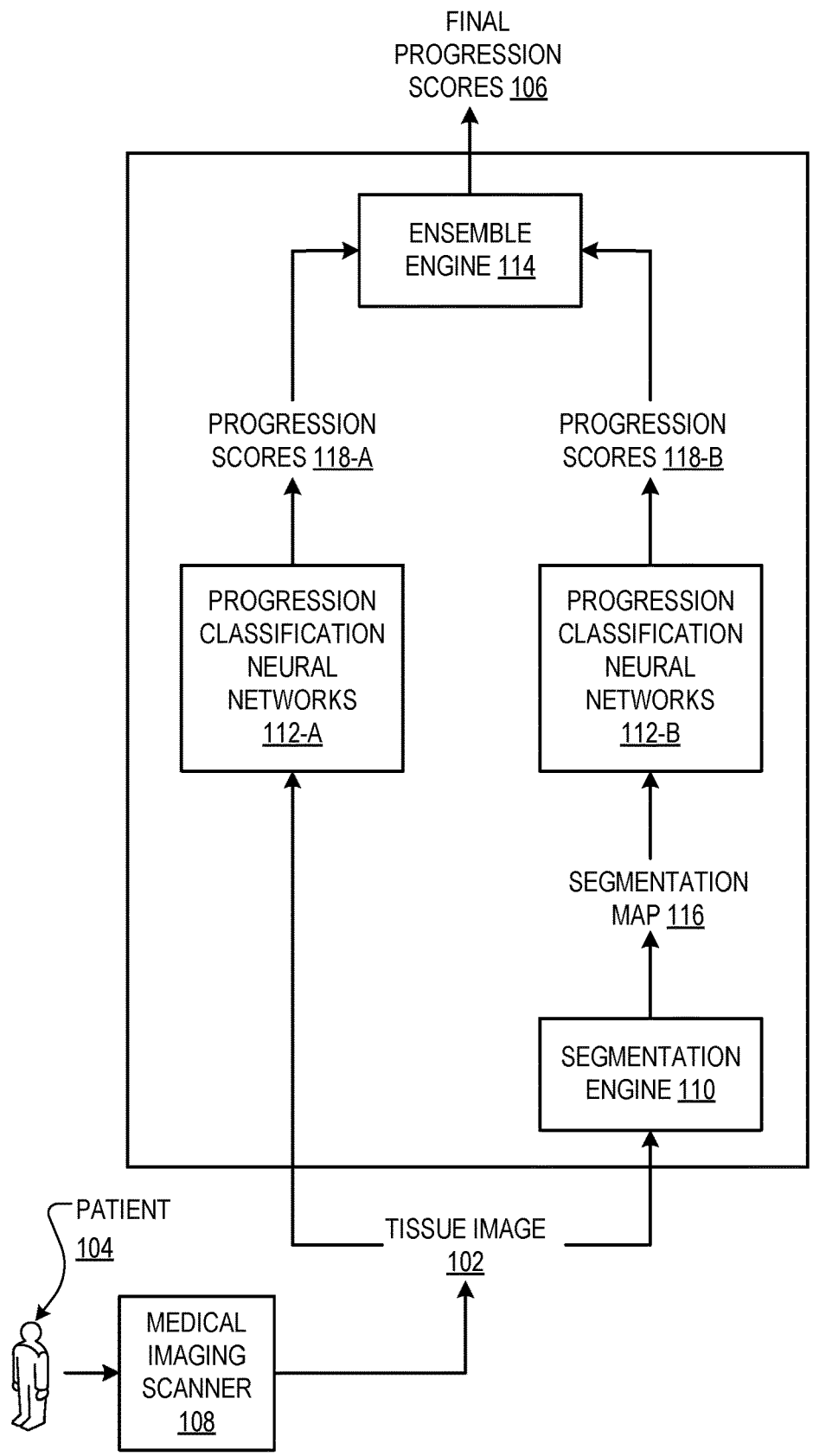
FIG. 1 shows an example disease progression prediction system.

FIG. 1 shows an example disease progression prediction system 100. The disease progression prediction system 100 is an example of a system implemented as computer programs on one or more computers in one or more locations in which the systems, components, and techniques described below are implemented.

The system 100 is configured to process a tissue image 102 depicting tissue in a region of the body of a patient 104 to generate a respective "final" progression score 106 for each of one or more future intervals of time. The final progression score 106 for a future interval of time characterizes a likelihood that the state of a medical condition affecting the tissue depicted in the tissue image 102 will progress to a target state in the future interval of time. Each future interval of time may be, e.g., an interval of time having a specified duration starting from a "current" time point, e.g., the time point when the tissue image 102 was captured. In one example, the system 100 may generate a respective final progression score 106 for future intervals of time having durations 3 months, 6 months, 9 months, and 12 months, starting from a current time point.

The tissue image 102 may be a two-dimensional (2D) image (e.g., represented as a 2D array of pixels), a three dimensional (3D) image (e.g., represented as a 3D array of voxels), or a higher dimensional image. The tissue image 102 can be acquired by a medical imaging scanner 108 using any imaging modality, e.g., the scanner 108 may be an optical coherence tomography (OCT) scanner, a magnetic resonance imaging (MRI) scanner, an X-ray scanner, a computed tomography (CT) scanner, an ultrasound (US) scanner, or a photographic scanner. The tissue image 102 may include multiple images depicting the tissue in the region of the body of the patient, e.g., that may be captured using different imaging modalities. The region of the body of the patient 104 depicted by the tissue image 102 may be, for example, an eye, a breast, a prostate, a brain, or the whole body.

The medical condition may be, e.g., age-related macular degeneration (AMD—i.e., affecting eye tissue), a form of cancer (e.g., breast cancer, prostate cancer, or liver cancer), Alzheimer's, dementia, Parkinson's disease, chronic kidney disease (CKD), or any other medical condition.

The medical condition may be associated with a predefined set of possible states, where the state of the medical condition may characterize any aspect of how the medical condition is affecting the patient. For example, the states of AMD may include: (i) an early, mild form of the condition, and (ii) a sight-threatening late form known as neovascular AMD (nAMD) or exudative wet AMD (exAMD). Optionally, the set of possible states of the medical condition may be understood to include a default "healthy" state, i.e., where the medical condition is not affecting the patient.

In a particular example, the tissue image 102 may be an OCT image depicting the tissue in an eye of the patient 104, and the final progression score 106 may characterize a likelihood that the eye tissue will progress from the early, mild form of AMD to sight-threatening nAMD (exAMD).

The system 100 may generate the final progression scores 106 using a segmentation engine 110, one or more progression classification neural networks 112-A (that process tissue images), one or more progression classification neural networks 112-B (that process segmentation maps of tissue images), and an ensemble engine 114, each of which will be described in more detail next.

The segmentation engine 110 is configured to process the tissue image 102 to generate a corresponding segmentation map 116, i.e., that segments the tissue image 102 into a predefined set of possible tissue classes. The segmentation map 116 may be a "hard" segmentation map or a "soft" segmentation map. A hard segmentation map associates each voxel of the tissue image 102 with a respective tissue class, while a soft segmentation map associates each voxel of the tissue image 102 with a respective probability of being included in each possible tissue class.

The segmentation map 116 may be represented, e.g., by a collection of "channels" including a respective channel corresponding to each possible tissue class, where the channel corresponding to a tissue class may be represented as an ordered collection of numerical values having the same size (dimensionality) as the tissue image 102. For a hard segmentation map, the value of each voxel of a channel may define whether the corresponding voxel of the tissue image 102 is included in the tissue class corresponding to the channel. For a soft segmentation map, the value of each voxel of a channel may define the probability that the corresponding voxel of the tissue image 102 is included in the tissue class corresponding to the channel.

The set of possible tissue classes may include, e.g., anatomical tissue classes (e.g., corresponding to healthy tissues), pathological tissue classes (e.g., corresponding to diseased tissues), and artifacts (e.g., distortions of the tissue image).

In a particular example, the tissue image 102 may be an OCT image depicting the tissue in an eye of the patient, and the segmentation map 116 may segment the tissue image into a set of possible tissue classes including one or more of: vitreous and subhyaloid space (i.e., the area above the internal limiting membrane not covered by other tissue classes), posterior hyaloid (i.e., the hyper-reflective membrane visible above the retina in cases of posterior vitreous detachment), epiretinal membrane (i.e., the hyper-reflective band seen on the inner surface of the retina), neurosensory retina (i.e., all layers and contents of the retina excepting certain pathological features), intraretinal fluid (i.e., areas of round or oval hyporeflectivity located within the neurosensory retina), subretinal fluid (i.e., hyporeflective areas in the subretinal space), subretinal hyperreflective material (i.e., areas of hyperreflectivity between the retinal and retinal pigment epithelium (RPE)), RPE (i.e., hyperreflective band underlying the neurosensory retina), drusenoid pigment epithelium detachment (i.e., PED—elevation of the RPE and without the presence of fibrovascular material), serous PED (i.e., dome-shaped elevation of the RPE relative to Bruch's membrane), fibrovascular PED (i.e., irregular elevations of the RPE relative to Bruch's membrane containing fibrovascular tissue), choroid and outer layers (i.e., area below the RPE not covered by other tissue classes), mirror artifact (i.e., artefact caused by patient anatomy out of the OCT frame being reflected back onto the OCT), clipping artifact (i.e., padding voxels introduced at the edges of the OCT slice during image processing), and blink artifact (i.e., absent information due to patient blink), amongst others. In some implementations the tissue classes include a hyper-reflective foci (HRF) tissue class, where hyper-reflective foci comprise well-circumscribed, dot- or oval-shaped lesions that are present within the intraretinal layers.

The segmentation engine 110 may generate the segmentation map 116 using a set of segmentation neural networks, where each segmentation neural network is configured to process a tissue image to generate a corresponding segmentation map that segments the tissue image into the predefined set of possible tissue classes. Each segmentation neural network may have been trained on a different set of training data, with differently initialized parameters, or both, from each other segmentation neural network. To generate the segmentation map 116, the segmentation engine 110 may process the tissue image 102 using each segmentation neural network to generate a respective "initial" segmentation map, and then combine (e.g., average) the initial segmentation maps to generate the segmentation map 116. Generating the segmentation map 116 using multiple segmentation neural networks may increase the accuracy and robustness of the segmentation map 116, e.g., because a misclassification error by one segmentation neural network for a particular voxel may be corrected by other segmentation neural networks that correctly classify the voxel.

In some implementations, rather than using segmentation neural networks, the segmentation engine 110 may generate the segmentation map 116 using other types of machine learning models, e.g., random forests or support vector machines (SVMs). Alternatively, rather than generating the segmentation map 116 using one or more machine learning models, the segmentation map 116 may be manually generated by a human expert (e.g., a physician) and provided to the system 100 as a input, i.e., along with the tissue image 102.

Each progression classification neural network 112-A is configured to process the tissue image 102 to generate a respective progression score 118-A corresponding to each of the one or more future intervals of time. The system 100 may include multiple progression classification neural networks 112-A, where each progression classification neural network 112-A may have been trained on a different set of training data, with differently initialized parameters, or both, from each other progression classification neural network 112-A. Therefore, each progression classification neural network 112-A may potentially generate a different progression score 118-A by processing the same tissue image 102.

Each progression classification neural network 112-B is configured to process the segmentation map 116 corresponding to the tissue image 102 to generate a respective progression score 118-B corresponding to each of the one or more future intervals of time. Each progression classification neural network 112-B may have been trained on a different set of training data, with differently initialized parameters, or both, from each other progression classification neural network 112-B. Therefore, each progression classification neural network 112-B may potentially generate a different progression score 118-B by processing the same segmentation map 116.

Optionally, the system 100 may generate additional progression scores 118-A and 118-B using test-time data augmentation i.e. data augmentation when the system is used in inference. More specifically, the system 100 may generate multiple respective versions of the tissue image 102 and the segmentation map 116 by applying transformation operations (e.g., random 3-D affine and elastic transformations) to the tissue image 102 and the segmentation map 116. The system 100 may process each version of the tissue image 102 using each progression classification neural network 112-A to generate respective progression scores 118-A, and the system 100 may process each version of the segmentation map 116 using each progression classification neural network 112-B to generate respective progression scores 118-B.

The ensemble engine 114 is configured to generate a respective final progression score 106 for each future interval of time by combining each of the progression scores 118-A and 118-B for the future interval of time. The ensemble engine 114 may combine the progression scores 118-A and 118-B for a future interval of time, e.g., by computing the average or the median of the progression scores 118-A and 118-B for the future interval of time.

The progression scores 118-A generated based on the tissue image 102 and the progression scores 118-B generated based on the segmentation map 116 may be different and complementary. For example, the progression scores 118-A generated based on the tissue image 102 may reflect image features not captured by the segmentation map 116 that may be relevant to the progression prediction task, e.g., patterns in the reflectivity of the tissue in an OCT image of an eye. The progression scores 118-B generated based on the segmentation map 116 may be more stable (i.e., less likely to assume inaccurate outlier values) than those generated using the tissue image 102, e.g., because of the potentially lower complexity of the segmentation map 116 relative to the tissue image 102. Therefore, generating the final progression scores 106 based on both the tissue image 102 and the segmentation map 116 may improve the performance, e.g., the accuracy and robustness, of the system 100.

The system 100 may provide the segmentation map 116 of the tissue image 102 to a user of the system 100 along with the progression scores for the medical condition. The segmentation map 116 may enable the user to better understand and interpret the rationale used by the system 100 to generate the progress scores, and thereby increase the confidence the user may place in the progression scores.

The final progression scores 106 generated by the system 100 may be used, e.g., as part of a clinical workflow to facilitate decision-making regarding whether and how to treat the patient 104 for the medical condition. For example, the final progression score 106 for a future interval of time (e.g., the next 6 months) being above a "treatment threshold" may be a relevant factor used to determine that preventative treatments should be administered to the patient, or that regular follow-ups should be performed to monitor the progression of the medical condition.

The treatment threshold may be determined, e.g., by using the system 100 to generate a respective final progression score 106 for a future time interval for each tissue image in a set of validation data. A tissue image may be included in the validation data if: (i) the progression neural networks were not trained on the tissue image, and (ii) it is known whether the state of the medical condition corresponding to the tissue image progressed to the target state in the future time interval. A treatment threshold may be selected from a range of possible treatment thresholds, e.g., to achieve a desired sensitivity and or specificity such as 90% specificity or 80% sensitivity. Sensitivity may refer to a ratio of: (i) the number of tissue images having a progression score above the treatment threshold and for which the state of the medical condition progressed to the target state in the future time interval, and (ii) the number of tissue images for which the state of the medical condition progressed to the target state in the future time interval. Specificity may refer to a ratio of: (i) the number of tissue images having a progression score below the treatment threshold and for which the state of the medical condition did not progress to the target state in the future time interval, and (ii) the number of tissue images for which the state of the medical condition did not progress to the target state in the future time interval.

Generally, the progression classification neural networks 112-A and 112-B, and the segmentation neural networks used by the segmentation engine 110, may have any appropriate neural network architecture that enables them to perform their described functions. For example, their respective architectures may include convolutional neural network layers, pooling neural network layers, fully-connected neural network layers, or a combination thereof, connected in any appropriate configuration. In one example, each progression classification neural network may include a sequence of "blocks", where each block includes a sequence of convolutional neural network layers having 3-D convolutional kernels with dimensionality 1×3×3 or 3×1×1, and where the output of the block includes a concatenation of the output of each convolutional neural network layer in the block. The last convolutional block may be followed by a fully-connected layer that outputs a respective progression score corresponding to each of one or more future time intervals. In another example, each segmentation neural network may have a 3-D U-Net neural network architecture.

The progression classification neural networks 112-A and 112-B and the segmentation neural networks may be trained on respective sets of training data to optimize an objective function (e.g., a cross-entropy objective function) using machine learning training techniques, e.g., stochastic gradient descent. For example, the progression classification neural networks may be trained on training examples that each include: (i) a training input, e.g., a training tissue image or a training segmentation map, and (ii) a respective target progression score for each of one or more future time intervals. The target progression score for a future time interval may be defined as the progression score that should be generated for the future time interval by a progression neural network by processing the training input. The target progression score for a future time interval may be represented, e.g., as a binary score 0/1 indicating if the medical condition progressed to the target state during the future time interval. As another example, the segmentation neural networks may be trained on training examples that each include: (i) a training tissue image, and (ii) a target segmentation map that should be generated by the segmentation neural networks by processing the training tissue image, e.g. derived from expert labelling.

Optionally, the progression classification neural networks may be trained to perform one or more "auxiliary" prediction tasks, i.e., by generating additional prediction outputs other than the progression scores. Generally, training the progression classification neural networks to perform auxiliary tasks may enable the progression classification neural networks to generate more effective internal representations of network inputs, and thereby achieve improved performance, e.g., prediction accuracy. A few examples of auxiliary prediction tasks are described in more detail next.

In one example, each progression classification neural network may generate a respective diagnosis score for each of one or more possible medical conditions that may be affecting the patient, where the diagnosis score for a possible medical condition characterizes a likelihood that the patient has the medical condition. Examples of possible medical conditions affecting the eye of a patient may include, e.g., macular retinal edema (MRO), choroidal neovascularization (CNV), and geographic atrophy.

In another example, each progression classification neural network may generate a referral score for each of multiple possible clinical referral decisions, where a clinical referral decision specifies an urgency with which the patient should receive further medical attention (e.g., by a specialist physician). The referral score for a referral decision may represent a predicted likelihood that the referral decision is the most appropriate referral decision for the patient. Examples of referral decision include: observation only, routine, semi-urgent, and urgent.

The progression classification neural networks may be trained to perform the auxiliary prediction tasks on a set of training data to optimize an objective function (e.g., a cross-entropy objective function) using machine learning training techniques, e.g., stochastic gradient descent. For example, the progression classification neural networks may be trained on training examples that each include: (i) a training input, e.g., a training tissue image or a training segmentation map, and (ii) target auxiliary scores, e.g., diagnosis or referral scores, that should be generated by the progression neural network by processing the training input. In some implementations, the system 100 may train the progression classification neural networks to perform auxiliary tasks using distillation training techniques. For example, the system 100 may generate the target auxiliary scores for training the progression neural networks based on the outputs of another neural network that is trained solely to perform the auxiliary prediction task.

The system 100 described in this specification is widely applicable, and can be applied to process various types of tissue images to generate progression scores for various medical conditions. In a particular example, the system 100 may be used to process an OCT image of an eye of a patient to generate a progression score characterizing a likelihood that the eye will progress from the early, mild or dry form of AMD (or from a healthy state) to sight-threatening nAMD (exAMD) within a 6-month period. Sight in an eye may be rapidly lost once nAMD develops and treatment of nAMD is most effective if administered soon after conversion, making the point of conversion from early AMD to nAMD (e.g. the treatment threshold) a critical moment in management of this disease. The system 100 can be used to identify patients with a significant likelihood of developing nAMD in an eye within a 6-month period, and these patients may have their eyes examined in regular follow-ups to diagnose and treat nAMD soon after it develops.

Figure 2:
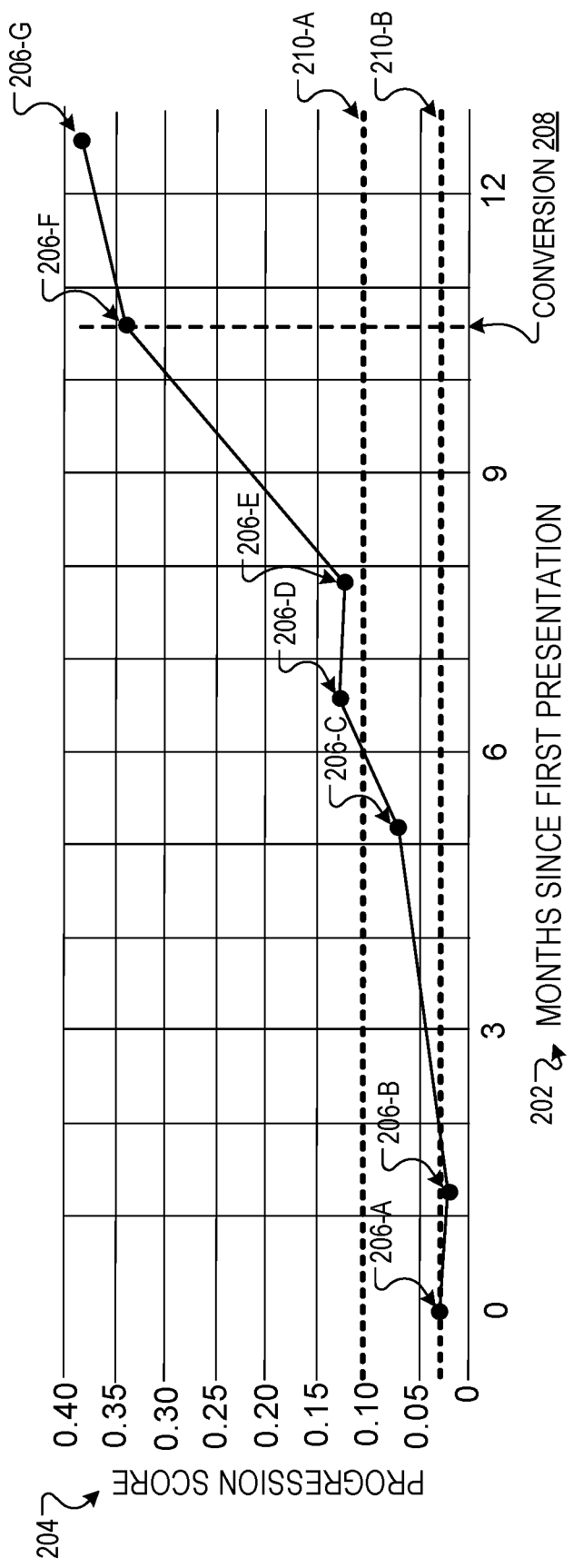
FIG. 2 illustrates predictions made by a disease progression prediction system by processing multiple OCT images of an eye of a patient over a period of months to generate progression scores characterizing a likelihood that the eye would progress from early AMD to nAMD within a 6-month period.

FIG. 2 illustrates predictions made by the system 100 by processing multiple OCT images of an eye of a patient over a period of months to generate progression scores characterizing a likelihood that the eye would progress from early or dry AMD to nAMD within a 6-month period. The horizontal axis 202 represents time (in months), the vertical axis 204 represents progression score values, and each circle 206-A-G represents a final progression score generated by the system 100 by processing an OCT image captured at the corresponding time point. The vertical line 208 represents the point of conversion of eye from early AMD to nAMD, and the horizontal lines 210-A-B represent possible treatment thresholds, i.e., such that a progression score above the treatment threshold indicates that nAMD is predicted to develop within a 6-month period. It can be appreciated that, using either treatment threshold, progression scores generated by the system 100 would enable accurate early prediction of the eventual conversion of the eye to nAMD, thereby enabling treatment to be commenced soon after conversion.

Figure 3:
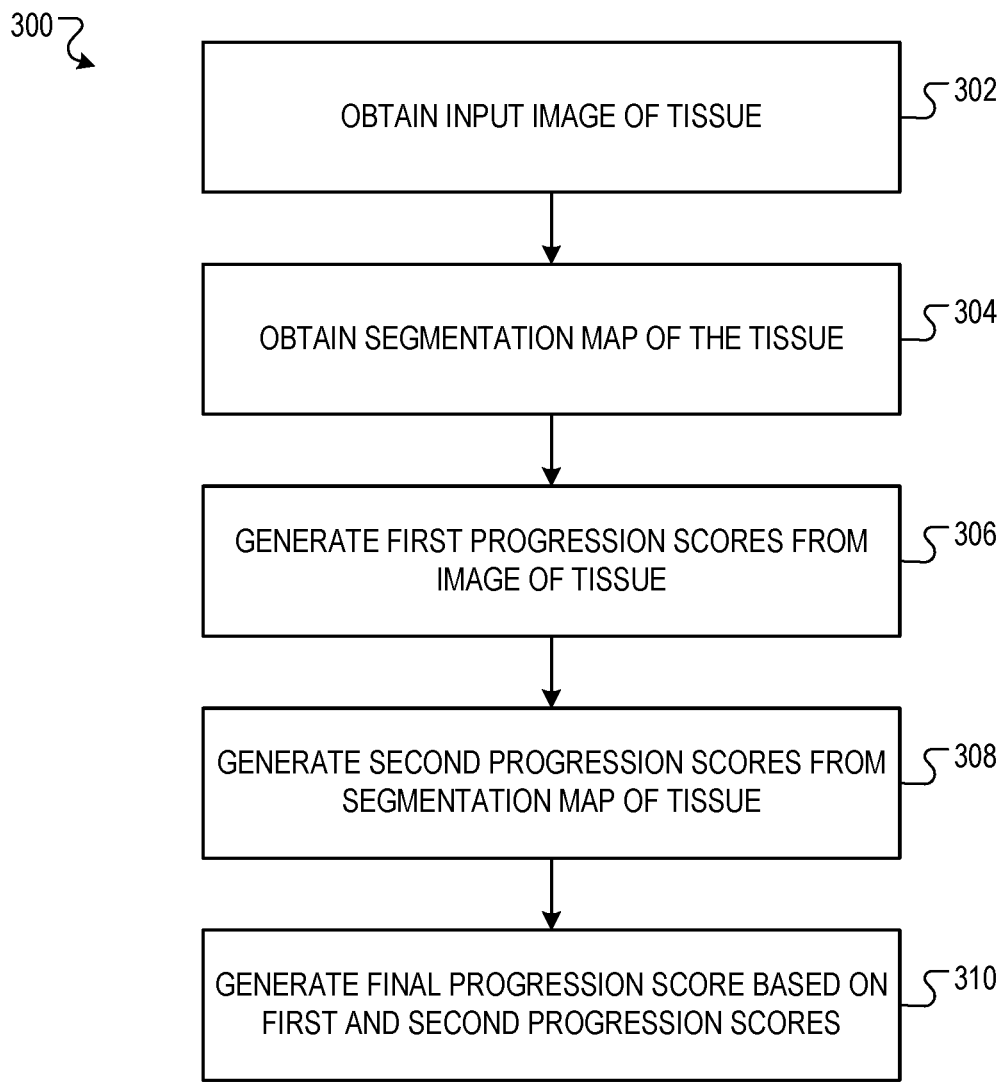
FIG. 3 is a flow diagram of an example process for generating a final progression score characterizing a likelihood that the state of a medical condition affecting a patient will progress to a target state in a future interval of time.

FIG. 3 is a flow diagram of an example process 300 for generating a final progression score characterizing a likelihood that the state of a medical condition affecting a patient will progress to a target state in a future interval of time. For convenience, the process 300 will be described as being performed by a system of one or more computers located in one or more locations. For example, a disease progression prediction system, e.g., the disease progression prediction system 100 of FIG. 1, appropriately programmed in accordance with this specification, can perform the process 300.

The system obtains an input image of tissue (e.g., eye tissue) captured using an imaging modality (302).

The system obtains a segmentation map of the tissue in the input image into multiple tissue types (304).

The system provides the input image to each of one or more first progression classification neural networks to obtain a respective first progression score from each first progression classification neural network (306). Each first progression classification neural network is configured to process an image of tissue captured using an imaging modality to generate a first progression score characterizing a likelihood that a state of a medical condition affecting the tissue will progress to a target state in the future interval of time.

The system provides the segmentation map to each of one or more second progression classification neural networks to obtain a respective second progression score from each second progression classification neural network (308). Each second progression classification neural network is configured to process a segmentation map of an image of tissue that segments the tissue in the image into multiple tissue types to generate a second progression score. Each second progression score characterizes a respective likelihood that a state of a medical condition affecting the tissue will progress to a target state in the future interval of time.

The system generates the final progression score based on the first progression scores and the second progression scores (310) e.g. by averaging the first progression scores and the second progression scores or by combining these in some other way.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising:
   one or more computers and one or more storage devices storing instructions that when executed by the one or more computers cause the one or more computers to implement:
   one or more first classification neural networks, wherein each first classification neural network is configured to:
      receive, by an input layer of the first classification neural network, an image of eye tissue captured using an imaging modality; and
      process the image to generate, by an output layer of the first classification neural network, a first progression score characterizing a likelihood that a state of a medical condition affecting the eye tissue will progress to a target state in a future interval of time;
one or more second classification neural networks, wherein each second classification neural network is configured to:
receive, by an input layer of the second classification neural network, a segmentation map of an image of eye tissue that segments the eye tissue in the image into a plurality of tissue types; and
process the segmentation map to generate, by an output layer of the second classification neural network, a second progression score characterizing a likelihood that a state of a medical condition affecting the eye tissue will progress to a target state in a future interval of time;
a subsystem configured to:
obtain: (i) an input image of eye tissue captured using an imaging modality, and (ii) a segmentation map of the eye tissue in the input image into a plurality of tissue types; and
generate, based on the input image and the segmentation map, a final progression score characterizing a likelihood that a state of a medical condition affecting the eye tissue will progress to a target state in a future interval of time, comprising:
providing the input image to each of the first classification neural networks to obtain a respective first progression score from each first classification neural network;
providing the segmentation map to each of the second classification neural networks to obtain a respective second progression score from each second classification neural network; and
generating the final progression score based on: (i) the first progression scores obtained based on the input image of eye tissue, and (ii) the second progression scores obtained based on the segmentation map.

2. The system of claim 1, wherein the imaging modality is an optical coherence tomography (OCT) modality.

3. The system of claim 1, wherein the medical condition affecting the eye tissue is age-related macular degeneration (AMD).

4. The system of claim 3, wherein the target state of the medical condition affecting the eye tissue is neovascular age-related macular degeneration (nAMD).

5. The system of claim 1, further comprising:
one or more segmentation neural networks, wherein each segmentation neural network is configured to:
receive an image of eye tissue captured using the imaging modality; and
process the image to generate a segmentation map of the image that segments the eye tissue in the image into a plurality of tissue types;
wherein the subsystem is further configured to:
provide the input image to each of the segmentation neural networks to obtain a respective initial segmentation map of the eye tissue in the input image into a plurality of tissue types from each segmentation neural network; and
generate the segmentation map based on the initial segmentation maps.

6. The system of claim 5, wherein generating the segmentation map based on the initial segmentation maps comprises averaging a plurality of the initial segmentation maps.

7. The system of claim 5, wherein each segmentation neural network is a convolutional neural network having a U-Net architecture.

8. The system of claim 1, wherein the input image of eye tissue captured using the imaging modality is a three-dimensional image comprising a plurality of voxels, and wherein the segmentation map assigns a respective tissue type from a predetermined set of tissue types to each of the voxels.

9. The system of claim 8, wherein the predetermined set of tissue types comprise one or more anatomical tissue types and one or more pathological tissue types.

10. The system of claim 1, wherein the future interval of time is an interval of time starting from a current time point.

11. The system of claim 1, further comprising generating, for each of a plurality of given future intervals of time, a respective final progression score characterizing a likelihood that the state of the medical condition affecting the eye tissue will progress to the target state in the given future interval of time.

12. The system of claim 1, further comprising determining, based on the final progression score, that preventative treatment should be administered to the eye tissue.

13. The system of claim 1, wherein the first classification neural networks and the second classification neural networks are trained to generate additional outputs characterizing referral decisions and additional diagnoses.

14. The system of claim 1, wherein:
the system comprises a plurality of first classification neural networks, wherein each first classification neural network has a same architecture but has been trained (i) on a different set of training data, (ii) with differently initialized parameters, or (iii) both, from each other first classification neural network.

15. The system of claim 1, wherein:
the system comprises a plurality of second classification neural networks, wherein each second classification neural network has a same architecture but has been trained (i) on a different set of training data, (ii) with differently initialized parameters, or (iii) both, from each other second classification neural network.

16. The system of claim 1, wherein providing the input image to each of the first classification neural networks and providing the segmentation map to each of the second classification neural networks comprises performing test-time data augmentation.

17. The system of claim 1, wherein generating the final progression score based on the first progression scores and the second progression scores comprises averaging the first progression scores and the second progression scores.

18. A method performed by one or more data processing apparatus, the method comprising:
obtaining: (i) an input image of eye tissue captured using an imaging modality, and (ii) a segmentation map of the eye tissue in the input image into a plurality of tissue types; and
generating, based on the input image and the segmentation map, a final progression score characterizing a likelihood that a state of a medical condition affecting the eye tissue will progress to a target state in a future interval of time, comprising:
providing the input image to each of one or more first classification neural networks to obtain a respective first progression score from each first classification neural network, wherein each first classification neural network is configured to:

receive, by an input layer of the first classification neural network, the input image of eye tissue captured using the imaging modality; and process the input image to generate, by an output layer of the first classification neural network, a first progression score characterizing a likelihood that a state of a medical condition affecting the eye tissue will progress to the target state in the future interval of time;

providing the segmentation map to each of one or more second classification neural networks to obtain a respective second progression score from each second classification neural network, wherein each second classification neural network is configured to:

receive, by an input layer of the second classification neural network, the segmentation map of the eye tissue in the input image into a plurality of tissue types; and process the segmentation map to generate, by an output layer of the second classification neural network, a second progression score characterizing a likelihood that a state of a medical condition affecting the eye tissue will progress to the target state in the future interval of time; and generating the final progression score based on: (i) the first progression scores obtained based on the input image of eye tissue, and (ii) the second progression scores obtained based on the segmentation map.

19. The method of claim 18, wherein the imaging modality is an optical coherence tomography (OCT) modality.

20. One or more non-transitory computer storage media storing instructions that when executed by one or more computers cause the one or more computers to perform operations comprising:

obtaining: (i) an input image of eye tissue captured using an imaging modality, and (ii) a segmentation map of the eye tissue in the input image into a plurality of tissue types; and generating, based on the input image and the segmentation map, a final progression score characterizing a likelihood that a state of a medical condition affecting the eye tissue will progress to a target state in a future interval of time, comprising:

providing the input image to each of one or more first classification neural networks to obtain a respective first progression score from each first classification neural network, wherein each first classification neural network is configured to:

receive, by an input layer of the first classification neural network, the input image of eye tissue captured using the imaging modality; and process the input image to generate, by an output layer of the first classification neural network, a first progression score characterizing a likelihood that a state of a medical condition affecting the eye tissue will progress to the target state in the future interval of time;

providing the segmentation map to each of one or more second classification neural networks to obtain a respective second progression score from each second classification neural network, wherein each second classification neural network is configured to:

receive, by an input layer of the second classification neural network, the segmentation map of the eye tissue in the input image into a plurality of tissue types; and process the segmentation map to generate, by an output layer of the second classification neural network, a second progression score characterizing a likelihood that a state of a medical condition affecting the eye tissue will progress to the target state in the future interval of time; and generating the final progression score based on: (i) the first progression scores obtained based on the input image of eye tissue, and (ii) the second progression scores obtained based on the segmentation map.

\* \* \* \* \*